(12) United States Patent
Eslava et al.

(10) Patent No.: US 10,361,508 B2
(45) Date of Patent: Jul. 23, 2019

(54) DOCKING DEVICES AND CABLE CONNECTORS FOR PATIENT MONITORING SYSTEMS

(71) Applicant: DRÄGERWERK AG & CO KGAA, Lübeck (DE)

(72) Inventors: Juan Pablo Eslava, Groton, MA (US); Ricardo L. Fernandez, Beverly, MA (US); Zachary K. Hennings, Reading, MA (US)

(73) Assignee: Drägerwerk AG & Co. KGaA (DE)

( * ) Notice: Subject to any disclaimer, the term of this patent is extended or adjusted under 35 U.S.C. 154(b) by 0 days.

(21) Appl. No.: 15/069,589

(22) Filed: Mar. 14, 2016

(65) Prior Publication Data

US 2017/0264045 A1    Sep. 14, 2017

(51) Int. Cl.
| | |
|---|---|
| *G02B 6/38* | (2006.01) |
| *G02B 6/36* | (2006.01) |
| *G02B 6/00* | (2006.01) |
| *H01R 13/62* | (2006.01) |
| *A61B 5/00* | (2006.01) |
| *H01R 13/64* | (2006.01) |

(52) U.S. Cl.
CPC .......... *H01R 13/6205* (2013.01); *A61B 5/00* (2013.01); *G02B 6/3886* (2013.01); *H01R 13/64* (2013.01); *A61B 2560/0456* (2013.01); *A61B 2562/225* (2013.01); *G02B 6/3817* (2013.01); *G02B 6/3831* (2013.01); *G02B 6/3895* (2013.01)

(58) Field of Classification Search
CPC .... H01R 13/6205; H01R 11/30; H01R 13/64; H01R 31/065; H01R 13/24; H01R 13/506; H01R 13/6683; H01R 13/40; H01R 13/73

USPC ...... 385/76–79, 86, 87, 92, 93, 134; 439/38, 439/39, 52, 218, 219, 221–223
See application file for complete search history.

(56) References Cited

U.S. PATENT DOCUMENTS

| | | | |
|---|---|---|---|
| 3,786,391 A | 1/1974 | Mathauser | |
| 3,808,577 A * | 4/1974 | Mathauser | ......... H01R 13/6205 439/180 |

(Continued)

FOREIGN PATENT DOCUMENTS

| | | |
|---|---|---|
| FR | 2938383 A1 | 5/2010 |
| WO | 92/16002 A1 | 9/1992 |
| WO | 02/41773 A1 | 5/2002 |

OTHER PUBLICATIONS

Patent Cooperation Treaty, International Search Report and Written Opinion for Application No. PCT/US2017/019874, dated May 24, 2017.

*Primary Examiner* — Kaveh C Kianni
*Assistant Examiner* — Hung Q Lam
(74) *Attorney, Agent, or Firm* — Design IP

(57) ABSTRACT

A connector includes a connector array of magnets having a first magnetic polarity pattern. A port includes a port array of magnets having a second magnetic polarity pattern that is complementary to the first magnetic polarity pattern. The connector is guided and aligned toward a mounted position in which the connector is retained on the port. The guiding and the aligning is through both (i) attraction when the connector is properly aligned to the port and (ii) repulsion when the connector is improperly aligned to the port. The port further includes a securing magnet configured to be activated when the connector reaches the mounted position, to magnetically secure the connector to the port.

38 Claims, 9 Drawing Sheets

(56) References Cited

U.S. PATENT DOCUMENTS

| | | |
|---|---|---|
| 7,311,526 B2 | 12/2007 | Rohrbach et al. |
| 7,658,613 B1 * | 2/2010 | Griffin .............. H01R 13/6205 |
| | | 439/39 |
| 8,348,678 B2 | 1/2013 | Hardisty et al. |
| 8,757,893 B1 | 6/2014 | Isenhour et al. |
| 8,970,332 B2 | 3/2015 | DiFonzo et al. |
| 9,219,403 B2 | 12/2015 | Evans |
| 2007/0141860 A1 * | 6/2007 | Hernandez ............. H01F 38/14 |
| | | 439/38 |
| 2009/0239392 A1 * | 9/2009 | Sumitomo ......... H01R 13/6205 |
| | | 439/39 |
| 2012/0155803 A1 | 6/2012 | Benjamin et al. |
| 2013/0136400 A1 | 5/2013 | Isenhour et al. |
| 2013/0279060 A1 * | 10/2013 | Nehl ....................... H01F 7/20 |
| | | 361/144 |
| 2014/0072261 A1 | 3/2014 | Isenhour et al. |

* cited by examiner

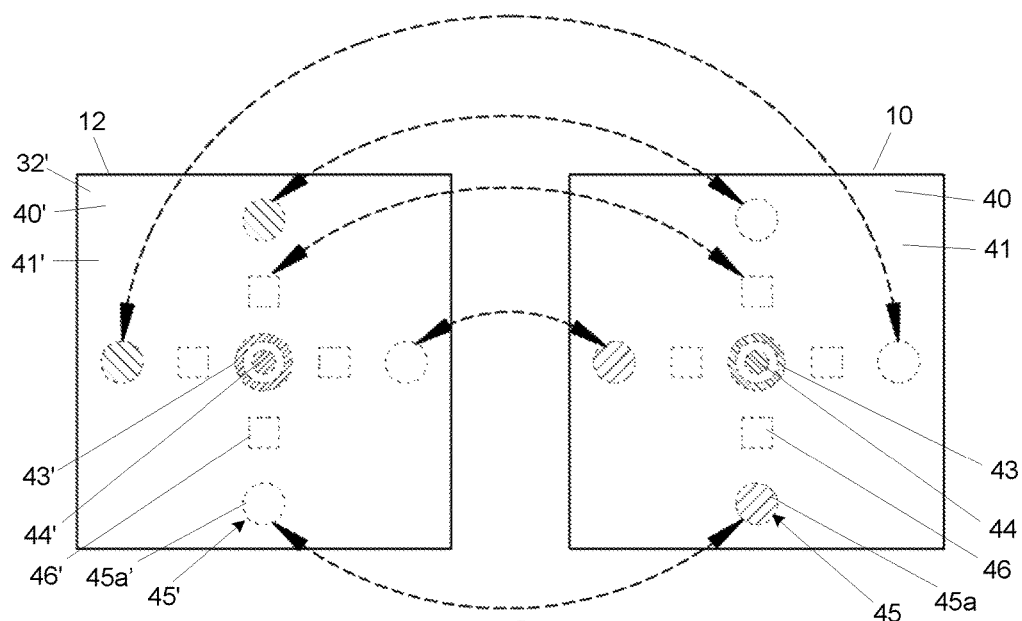
FIG. 4
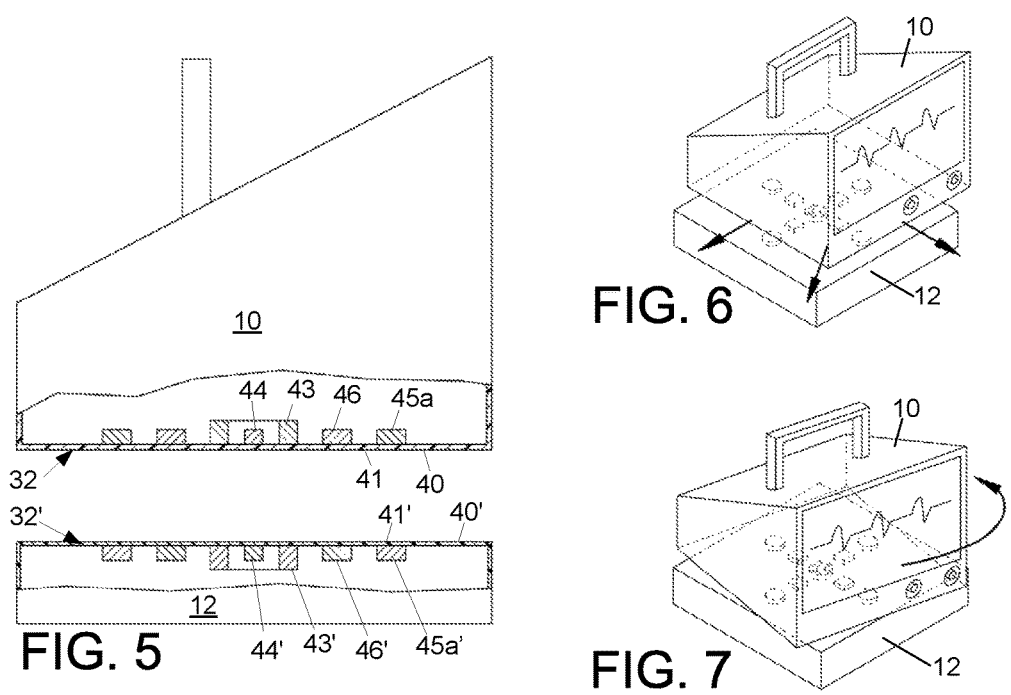
FIG. 5
FIG. 6
FIG. 7

DOCKING DEVICES AND CABLE CONNECTORS FOR PATIENT MONITORING SYSTEMS

TECHNICAL FIELD

The subject matter described herein relates to implementing magnets, for example multi-pole correlated magnetic structures, in docking devices and cable connectors for patient monitoring devices and docking stations.

BACKGROUND

A patient monitoring apparatus includes a patient monitoring device (patient monitor) that is docked on a docking station. The docking station provides the patient monitor with stability, electrical power and a communication link. The patient monitor is connected to cables. At one end of each cable is a patient-end terminal configured to be coupled to a patient. At the opposite end of the cable is a cable connector configured to be connected to the patient monitor.

Conventional connection mechanisms for connecting a connector of one device to a connection port of another—a cable connector to a patient monitor port, and patient monitor connector to a docking station port—include keying and latching components. Keying and latching components require a user to place a connector in proper position relative to the port and rotate the connector into proper orientation relative to the port. This, in turn, requires a user to scrutinize first the connector to determine both its current orientation and a correct direction to rotate it.

Keying and latching components can contribute gaps and structural complexity. The gaps and structural complexity increase the difficulty of cleaning the ports and connectors. Furthermore, wear of moving parts of the latching components can reduce working life of the ports and connectors. Also, each connector is designed to match a correspondingly-designed port, which reduces the port's flexibility in accepting differently-designed connectors.

SUMMARY

In one aspect, an apparatus includes a port having a port array of magnets and a securing magnet. The port is configured for connection with a connector that includes a connector array of magnets having a connector magnetic polarity pattern. The port array of magnets has a port magnetic polarity pattern that is complementary to the connector magnetic polarity pattern so as to guide and align the connector toward a mounted position in which the connector is retained on the port. The guiding and the aligning may be through both (i) attraction when the connector is properly aligned to the port and (ii) repulsion when the connector is improperly aligned to the port. The securing magnet is configured to be activated when the connector reaches the mounted position, to magnetically secure the connector to the port.

In some variations, the apparatus may further include the connector.

The connector may be configured to be secured to the port solely by (i) magnetic force between the connector array and the port array and (ii) magnetic force of the securing magnet.

The connector may include a permanent magnet securing component that is configured to be attracted to the securing magnet when the securing magnet is activated to have a first polarity and to be repelled from the securing magnet when the securing magnet is activated to have an opposite second polarity.

The connector may include a connector terminal and the port may include a corresponding port terminal for communicating signals between the port terminal and the connector terminal. The connector may include a connector protective wall behind which the connector array and the connector terminal are located.

The apparatus may also include a port axis that is fixed relative to the port and a connector axis that is fixed relative to the connector such that the port and the connector are together configured to require the axes to be collinear while the connector moves toward and into the mounted position, while enabling the connector to rotate about the axes.

The port and the connector may together include a tab-in-recess configuration that is configured to enable linear movement of the connector toward and into the mounted position on the port while preventing lateral and rotational movement of the connector relative to the port.

The attraction between the port array and the connector array may be tactile.

The apparatus can further include a securing magnet controller that, in turn, may include an electromagnet that is configured to be activated by the securing magnet controller electrically energizing the securing magnet to secure the connector. The securing magnet may be configured to release the connector by being electrically de-energized. The securing magnet may be configured to repel the connector by the securing magnet controller reversing activation current through the securing magnet.

The securing magnet controller may be configured to (i) activate the securing magnet to have a first magnetic polarity to secure the connector to the port, and (ii) reverse the polarity of the securing magnet to magnetically repel the connector from the port.

The securing magnet controller may be configured to activate the securing magnet automatically in response to the connector reaching the mounted position.

The securing magnet controller may be configured to activate the securing magnet automatically in response to a human action.

The securing magnet may include a movable permanent magnet configured to be activated by being moved toward the connector and configured to be deactivated by being moved away from the connector.

The port may include a port terminal for communicating signals (e.g., electrical, optical, electro-optical, etc.) between the port and the connector. The port may include a protective wall behind which the port array the securing magnet and the port terminal are located. The port terminal may be one of a spiral array of port terminals that the port has for communicating signals between the port and the connector.

The magnets in the port array may be narrower than 2 mm.

The magnets of the port array may be electromagnets and activated by a port array controller.

The port array controller may be configured to adjust magnetic field strength of one or more of the port array's magnets individually. The port array controller may be configured to reverse magnetic polarity of one or more of the port array's magnets to repel the connector array.

The port magnetic polarity pattern may be a first port magnetic polarity pattern such that the port array controller may be configured to change magnetic polarities of the port array to a second port magnetic polarity pattern, different from the first port magnetic polarity pattern, that is configured to not provide the attraction to the port array.

The port may be part of a patient monitoring device. In such cases, the port array controller may be configured to change the magnetic polarities of the port array to the second port magnetic polarity pattern based on a device setting and/or a device state of the patient monitoring device. The connector may be a first connector and the apparatus may further include a second connector that includes a second connector array of magnets having a second connector magnetic polarity pattern that is complementary to the second port magnetic polarity pattern, so as to guide and align the second connector, through both (i) attraction when the second connector is properly aligned and (ii) repulsion when the second connector is improperly aligned, toward a predetermined mounted position against the port.

The port may include a cylindrical recess that surrounds and bounds a planar front surface such that a signal terminal may be located along the front surface, and the port array may be located behind a recessed surface at a bottom of the recess.

The port array may extend along a port array plane, and the connector array may extend along a connector array plane. With such variations, the apparatus may be configured to constrain the port array plane and the connector array plane to be parallel with each other and parallel with direction of movement of the connector toward and into the mounted position on the port.

The guiding and aligning may be sufficiently strong to move the connector into the mounted position automatically without manual interaction.

The port may form a part of one or more of a patient monitor, a cable, or a docking station.

The connector may form a part of one or more of a patient monitor, a cable, or a docking station.

The apparatus may include a ferromagnetic movable component that is urged by a spring bias into a retracted position, and that is configured to be attracted by a magnet in the port to move, against the spring bias, into an extended position when the connector is in the mounted position. The movement of the ferromagnetic movable component may be configured to open or close an electrical circuit. The ferromagnetic movable component may be in the port and/or in the connector.

One or more of the port array's magnets may include an electropermanent magnet. The securing magnet may be an electropermanent magnet.

In an interrelated aspect, a connector configured for connection with a port that includes a port array of magnets having a port magnetic polarity pattern and a securing magnet includes a connector array of magnets and a securing component. The connector array of magnets may have a connector magnetic polarity pattern that is complementary to the port magnetic polarity pattern so as to guide and align the connector toward a mounted position in which the connector is retained on the port such that the guiding and the aligning may be through both (i) attraction when the connector is properly aligned to the port and (ii) repulsion when the connector is improperly aligned to the port. The securing component may be configured to be magnetically secured to the securing magnet of the port when the connector reaches the mounted position. The connector, in such a variation, may be configured to be secured to the port solely by magnetic force. In other variations, the connector may be configured to be secured to the port solely by (i) magnetic force between the connector array and the port array and (ii) magnetic force between the connector's securing component and the port's securing magnet.

The securing component may include ferromagnetic material that is configured (i) to be attracted to and secured to the securing magnet when the securing magnet is activated and (ii) to be released from the securing magnet when the securing magnet is deactivated.

The securing component may include a permanent magnet that is configured to be attracted to the securing magnet when the securing magnet has a first polarity and to be repelled from the securing magnet when the securing magnet has an opposite second polarity.

The connector may include a connector terminal for communicating signals (e.g., electrical, optical, electro-optical, etc.) between the connector terminal and the port.

The connector may include a connector protective wall behind which the connector array, the securing component and the port terminal are located.

The connector terminal may be one of a spiral array of connector terminals that the connector has for communicating signals between the port and the connector.

The magnets of the connector array may be narrower than 2 mm.

The port may include a cylindrical recess that is surrounded by front surface such that the connector array is located behind the front surface an a signal terminal is located behind a bottom of the recess.

The connector array may extend along a connector array plane. In such a variation, the connector may be configured to constrain the connector array plane to be parallel with direction of movement of the connector toward and into the mounted position on the port.

The connector may form part of a patient monitor, a cable, and/or a docking station. If the connector forms part of a cable, the cable may be configured for patient monitoring and have a patient-end terminal configured to be coupled to a patient.

The connector may include a ferromagnetic movable component that is in the connector and is urged by a spring bias into a retracted position, and that is configured to be attracted by a magnet in the port to move, against the spring bias, into an extended position when the connector is in the mounted position. The movement of the ferromagnetic movable component may be configured to open or close an electrical circuit.

One or more of the connector array's magnets can include an electropermanent magnet.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

FIG. 4 includes a top view of the docking station and a bottom view of the patient monitor, indicating which components of the patient monitor interface with which components of the docking station.

FIG. 5 is a side sectional view of the docking station and the patient monitor.

FIG. 6 is a perspective view illustrating repositioning the patient monitor on the docking station.

FIG. 7 is a perspective view illustrating rotating of the patient monitor on the docking station.

DETAILED DESCRIPTION

Figure 1:
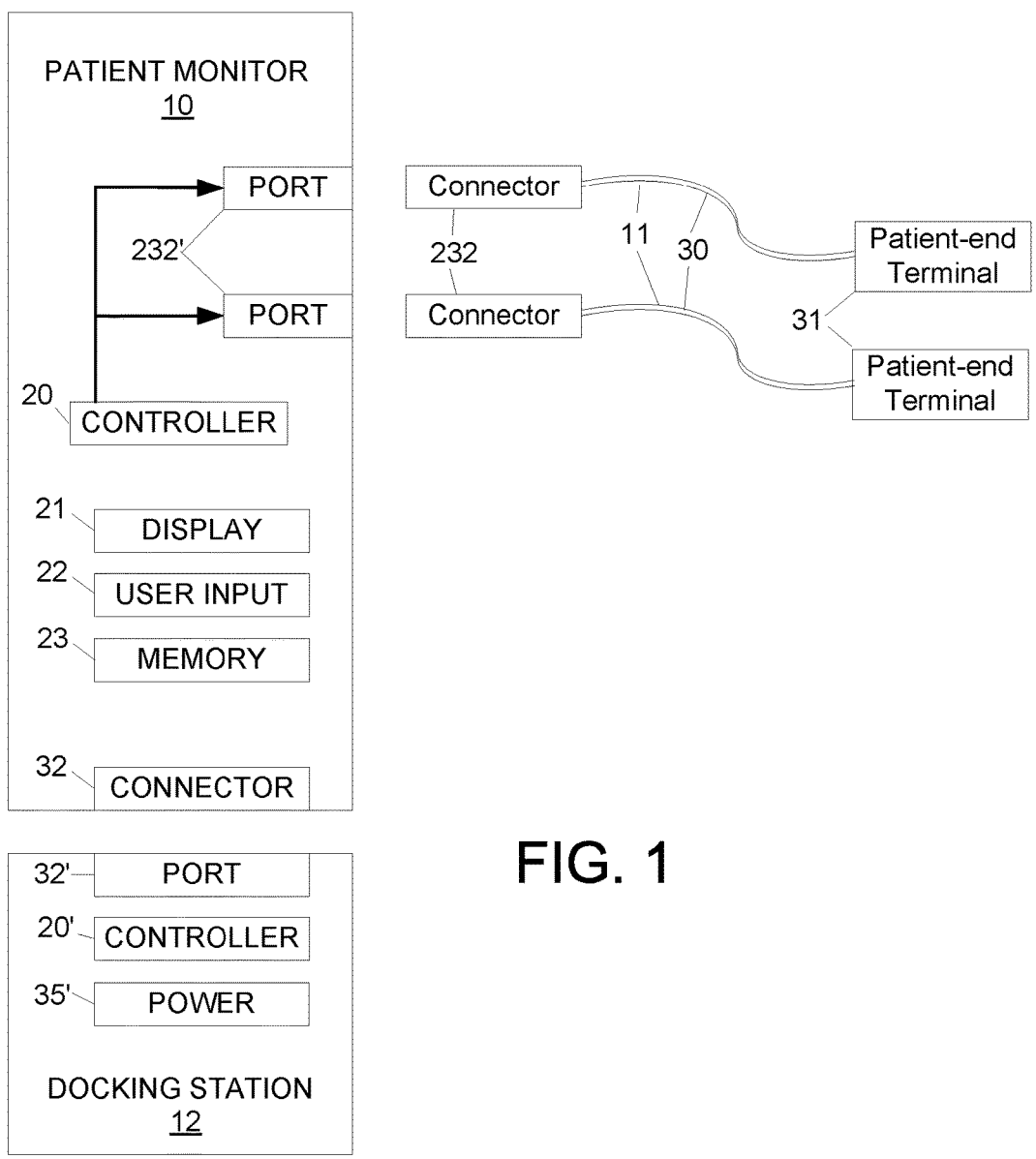
FIG. 1 is a block diagram of an example patient monitoring apparatus, including a patient monitor, a docking station and cables.
Figure 2:
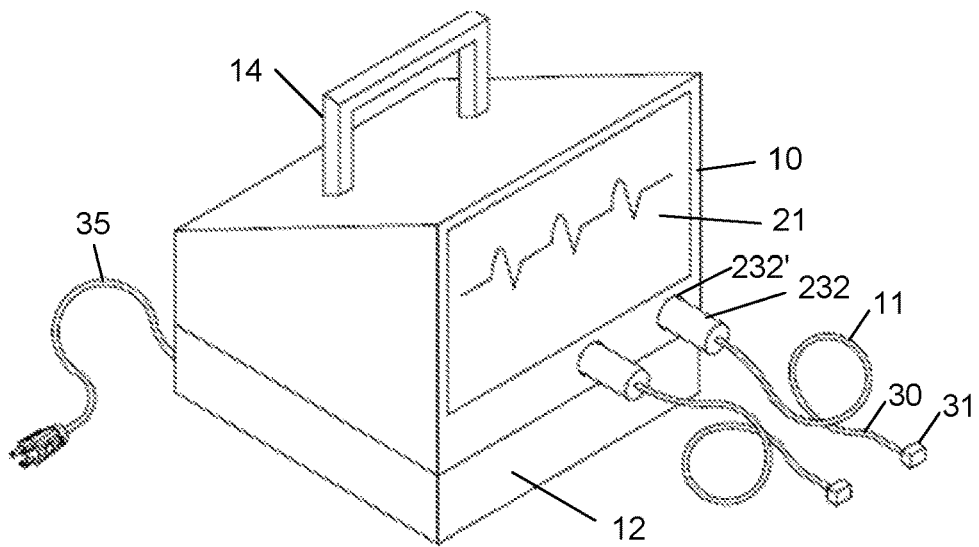
FIG. 2 is a perspective view of the apparatus in an assembled configuration, in which the cables are connected to the patient monitor and the patient monitor is mounted on the docking station.

FIG. 1 is a schematic view of an example patient monitoring apparatus. FIG. 2 is a perspective view of the apparatus. The apparatus includes a patient monitoring device 10 (hereinafter patient monitor). Examples of patient monitors and corresponding docking stations are described in U.S. patent application Ser. No. 14/414,409 published as U.S. Pat. Application Publication No. 2015/0243148, entitled "Portable Patient Monitoring System Profile Switchover", and U.S. Pat. No. 6,221,012 entitled "Transportable Modular Patient Monitor With Data Acquisition Modules", both documents are hereby incorporated herein by reference. Different cables 11 are configured to be connected to the patient monitor 10. A docking station 12 (base) secures the patient monitor 10 in place and provides electrical power to the patient monitor 10. The patient monitor 10 is configured to be magnetically aligned with, and magnetically secured to, the docking station 12. Similarly, each cable 11 is configured to be magnetically aligned with, and magnetically secured to the monitoring device 10.

In this example, the patient monitor 10 measures different physiological parameters (e.g., ECG, respiration, pulse rate, temperature, blood pressure, SpO2). For this purpose, one cable 11 might include a temperature sensor, and another cable 11 might include an ECG electrode.

The patient monitor 10 includes a processor-based controller 20 that monitors and controls all functions of the patient monitor 10. The patient monitor 10 displays the parameters on the patient monitor's display screen 21, enters user input through a user input device (which in this example is a virtual touch-pad function of the display screen 21), and records the parameters in the patient monitor's memory 23. The patient monitor 10 also outputs the parameters, along with other data, through a patient monitor connector 32 to the docking station 12, and inputs instructions, along with other data, through a patient monitor connector 32 from the docking station 12. The patient monitor 10 is portable, and has a handle 14 configured to be manually grasped for manually carrying the patient monitor 10.

Each cable 11 includes a flexible cable line 30 (lead). At one end of the cable line 30 is a patient-end terminal 31 (portrayed in the figures schematically as a box) to be attached to a patient. Examples of a patient-end terminal 31 are an oximeter sensor to be clipped to the patient's finger and an ECG (electrocardiogram) electrode to be adhered to the patient's skin. At the opposite end of each cable line 30 is a cable connector 232. The cable line 30 may include metallic electrical wires for conveying electrical signals and electrical power between the patient-end terminal 31 and the cable connector 232. Also, the cable line 30 may include optical fibers for conveying optical signals between the patient-end terminal 31 and the connector 232.

The docking station 12 includes a processor-based controller 20' that monitors and controls all functions of the docking station 12. The docking station 12 may be coupled to a communication network (e.g., an intranet or the Internet) and forward communications between the patient monitor 10 and the network. The docking station 12 also has a docking station port 32' (connection port), configured to magnetically attract and secure the patient monitor connector 32. In this example, the docking station port 32' is at a top surface of the docking station 12, and the patient monitor connector 32 is at a bottom surface of the patient monitor 10, for the patient monitor 10 to overlie the docking station 12. In another example, the docking station port 32' and patient monitor connector 32 might be located along respective side surfaces of the docking station 12 and the patient monitor 10, for the docking station 12 and the patient monitor 10 to be magnetically secured together side-by-side. In yet another example, the docking station port 32' might be along a bottom surface of the docking station 12, and the patient monitor connector 32 might be along a top surface of the patient monitor 10, for the patient monitor 10 to be suspended from, and magnetically secured to, the bottom of the docking station 12.

Figure 3:
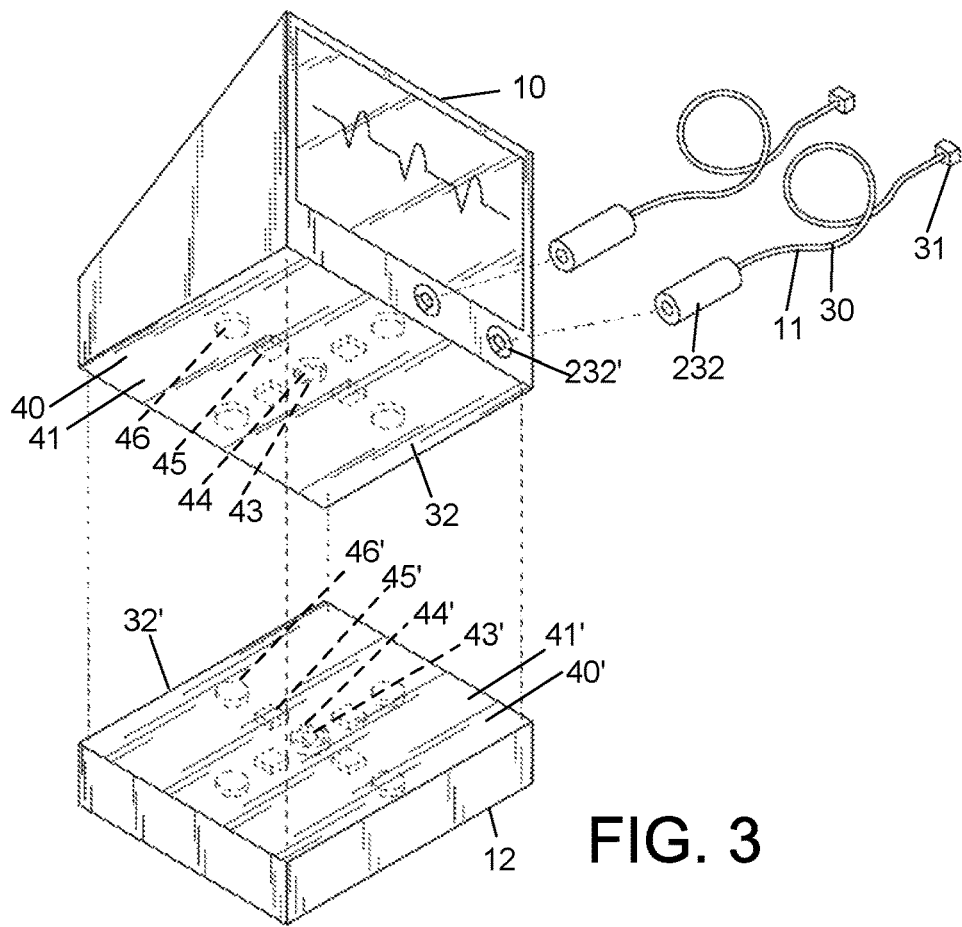
FIG. 3 is a perspective view of the apparatus in a disassembled configuration, in which the cables are disconnected from the patient monitor and the patient monitor is removed from the docking station.

As shown in FIGS. 3-5, the patient monitor connector 32 includes a flat (planar) protective wall 40, comprising a section of the bottom surface of the patient monitor 10. The protective wall 40 protects magnetic and electrical components of the patient monitor 10 and is electrically insulating. The protective wall 40 defines a washable protective surface 41 (interface surface). To enable magnetic coupling between the patient monitor connector 32 and the docking station port 32', the protective wall 40 of the patient monitor connector 32 may be thin and yet structurally sound.

Behind a transparent section (optical window) of the patient monitor connector's protective wall 40 is an optical terminal 44 (fiber optic termination), for sending and receiving optical (e.g., infrared) signals.

An induction receiver 43, e.g., comprising a pick-up coil, is configured to inductively generate electrical current from a varying magnet field. The inductively generated current may be used to power electrical components of the patient monitor 10, such as the controller 20 and an electrical power supply to the cables 11. The induction receiver 43 is located behind the patient monitor connector's protective wall 40 and may, as in this example, surround the patient monitor connector's optical terminal 44.

An array 45 of magnets 45a, behind the patient monitor connector's protective wall 40, has a predetermined pattern of magnetic polarities. This magnetic polarity pattern defines the positions of the forward-facing poles of the magnets 45a. The magnetic polarity pattern might also define the magnetic field intensity (field strength) of each pole, which might be different for different array magnets 45a within the array 45. In this example, the connector's array magnets 45a are separate permanent magnets.

In another example, the patient monitor connector's array magnets 45a might comprise different regions (magnet pixels, called maxels) of a single piece of magnetizable material, to form a multi-pole correlated magnetic structure in which the regions differ from each other in terms of magnetic polarity and/or magnetic strength. In yet another example, some or all of the array magnets 45a might be electromagnets—such as electrically activated coils that are activated (controlled) by the patient monitor's controller 20. The array magnets 45a might be narrower than 2 mm, and might be spaced apart by less than 3 mm.

One or more securing components 46, behind the patient monitor connector's protective wall 40, are configured to be attracted by a securing magnet in the docking station port 32'. In this example, each of the securing components 46 is a piece of ferromagnetic material (e.g., steel). Alternatively, each securing component 46 might be a magnet, such as a permanent magnet or electromagnet.

The docking station port 32', like the patient monitor connector 32, includes a flat (planar) protective wall 40', comprising a section of a top wall of the docking station 12. The protective wall 40' protects magnetic and electrical components of the docking station port 32' and is electrically insulating. The docking station port's protective wall 40' defines a washable protective surface 41' (interface surface). To enable magnetic coupling between the patient monitor connector 32 and the docking station port 32', the protective wall 40' of the docking station port 32' may be thin and yet structurally sound.

The protective surfaces 41, 41' of the patient monitor connector 32 and the docking station port 32' are configured to interface with each other in that, when the patient monitor connector 32 is mounted (docked) on the docking station port 32', the protective surfaces 41, 41' are facing and near (adjacent) each other, and possibly in contact with each other. Dashed double-ended arrows in FIG. 4 indicate which components of the patient monitor connector 32 interface with (interact with or contact) which components of the docking station port 32'.

Behind a transparent section (optical window) of the docking station port's protective wall 40' is an optical terminal 44' (fiber optic termination) for communicating optical signals to and from the patient monitor connector's optical terminal 44. A magnetic field source 43' generates the variable magnetic field (e.g., a coil powered by alternating current) from which the connector's induction receiver 43 (e.g., receiver coil) inductively generates electricity. The magnetic field source 43' may convert a mains voltage into a high frequency alternating current which is then delivered to a transmitter coil of the magnetic field source 43'. The high frequency alternating current may then induce a time varying magnetic field onto the induction receiver 43. The magnetic field source 43' is located behind the docking station port's protective wall 40' and may, as in this example, surround the docking station port's optical terminal 44'.

An array 45' of magnets 45a', behind the docking station port's protective wall 40', has a magnetic polarity pattern. This magnet polarity pattern of the docking station port's magnet array 45' is complementary to (correlates with) the polarity pattern of the patient monitor connector's magnet array 45, in that the docking station port's polarity pattern is a mirror image (flipped image) of the patient monitor connector's polarity pattern and each north pole of the patient monitor connector's polarity pattern is configured to face and align with a south pole of the docking station port's polarity pattern, and each south pole of the patient monitor connector's polarity pattern is configured to face and align with a north pole of the docking station port's polarity pattern. This is for the magnet arrays 45, 45' to magnetically interact to attract and guide the patient monitor connector 32 toward a predetermined mounted position (aligned position) on the docking station port, and to positionally (e.g. arrows in FIG. 6) and rotationally (e.g., changing orientation, arrow in FIG. 7) align the patient monitor connector 32 with the docking station port 32', and thus also the patient monitor 10 with the docking station 12.

The docking station port's array magnets 45a' in this example are separate permanent magnets. In another example, the port's array magnets 45' might comprise different regions (maxels) of a single piece of magnetizable material, to form a multi-pole correlated magnetic structure in which the regions differ in terms of magnetic polarity and/or magnetic field strength. In yet another example, some or all of the docking station port's array magnets 45' might be electromagnets—such as electrically activated coils that are activated (controlled) by the docking station's controller 20'. The port's array magnets 45a might be narrower than 2 mm, and might be spaced apart by less than 3 mm.

The magnetic guiding and aligning might be through either or both (i) attraction when the patient monitor connector 32 is properly positioned and aligned and (ii) repulsion when the patient monitor connector 32 is improperly positioned or improperly aligned. The guiding and aligning might be tactile in that the guiding and aligning would be sensed (felt) by a person (user) that is connecting the patient monitor 10 to the docking station 12. The magnetic guiding and aligning might simulate (provide the user with a tactile feel of) a conventional spring mechanism, detente mechanism or keying mechanism, that tactilely indicates to the person whether the patient monitor 10 is or is not oriented properly, and perhaps indicates to the person which direction to reposition (relocate, arrows in FIG. 6) or rotate (arrow in FIG. 7) the patient monitor 10, and perhaps provides a tactile feeling of reaching a detente position when the mounted position is reached.

In another example, the magnetic guiding and aligning might be sufficiently strong to move—such as reposition and rotate—the patient monitor toward and into the mounted position automatically without manual (i.e., human) assistance (e.g., without the user even touching the patient monitor).

As shown in FIGS. 3-5, one or more securing magnets 46', in this example electromagnets, are located behind the docking station port's protective wall 40', are connected to (controlled by) the docking station controller 20'. The docking station controller 20' activates (energizes) the securing magnets 46' when the patient monitor connector 32 reaches its mounted position on the docking station port 32'. This magnetically secures the patient monitor connector 32 to the docking station port 32' through magnetic attraction between the docking station port's securing magnets 46' and the patient monitor connector's securing components 46.

In this example, where the securing components 46 are pieces of ferromagnetic material, the patient monitor connector 32 is released from docking station port 32' when the securing magnets 46' are deactivated (de-energized) by cessation of electrical current. Alternatively, in the example described above where the securing components 46 are permanent magnets, the securing components 46 might be (i) initially attracted to the securing magnets 46' when the securing magnets 46' are activated (energized) by the controller 20' to have a first polarization, and (ii) later repelled by the securing magnets 46' when the securing magnets 46' are activated by the controller 20' (e.g., by the controller reversing the electrical activation current) to have an opposite second polarity. The magnetic repulsion might be stronger than the magnetic attraction between the magnet arrays 45, 45', so as to overcome the magnetic attraction between the magnet arrays 45, 45'. If the docking station port's array magnets 45a' are electromagnets controlled by the docking station controller 20', then the docking station controller 20' can reverse the magnetic polarities of some or all of the docking station port's array magnets 45a' in order to repel the patient monitor connector array 45.

The docking station controller 20' might activate the securing magnets 46' in response to the docking station controller 20' determining that the patient monitor's connector 32 has reached its mounted position. The docking station controller's determination that the patient monitor's connector 32 has reached its mounted position might be through optical means. For example, the docking station port's optical terminal 44' may include a photodetector and infrared (IR) light source to detect changes in ambient light and send a signal to confirm presence of the patient monitor connector 32. In turn, the patient monitor connector 32 might acknowledge its presence with a return signal, which would prompt the docking station controller 20' to activate the securing magnets 46'. The determination that the patient monitor's connector 32 has reached its mounted position might also be through means of a magnetic field sensor. For example, a Hall effect sensor may be located in the docking station port 32' and sense the magnetic field of the patient monitor's magnet array 45 as the patient monitor 10 approaches. Any disturbance in the magnetic field beyond a predefined threshold may prompt the docking station controller 20' to activate the securing magnets 46'. Or the controller 20' might activate the securing magnets 46' in response to a human action, for example input by a user (who is using the patient monitor 10), such as by the user pressing a button on the patient monitor 10. The docking station controller 20' might release the patient monitor connector 32 in any of the ways described above, in response to automatically determining that a test is completed or in response to a human action (e.g., input by a person using the patient monitor 10).

If the docking station port's array magnets 45a' are electromagnets, then the magnetic polarity pattern can be reprogrammed by the docking station controller 20' at different moments in time. For example, there might exist different patient monitors, each having a patient monitor connector with a unique magnetic polarity pattern. The docking station port 32' might be programmed (by the docking station controller 20') to complement—and thus attract—only a particular one of the patient monitor connectors at one moment in time and to be later reprogrammed to attract only another one of the patient monitor connectors. For the docking station port's array magnets 45a' to be programmable, the docking station controller 20' might be able to reverse the polarity of each array magnet 45a' individually by reversing the direction of electrical supply current to that magnet 45a'. The docking station controller 20' might also adjust magnetic field strength of each array magnet 45a' individually, by adjusting the magnitude of the electrical supply current to that array magnet 45'.

FIGS. 8A, 8B and 9-10 illustrate the example cable connector 232 and a corresponding patient monitor port 232'.

The cable connector 232 is centered on a first axis A, about which walls and surfaces of the cable connector 232 are symmetric. First axis A is fixed relative to the cable connector 232. The cable connector 232 includes a rigid insulating protective wall 240 that protects components inside the cable connector 232. The cable connector's protective wall 240 provides (i) a cylindrical radially-outer surface 241a facing radially-outward, (ii) a cylindrical radially-inner surface 241b facing radially-inward, (iii) an annular forward-facing front surface 241c, and (iv) a forward-facing recessed surface 241d. The radially-inner surface 241b and the recessed surface 241d together define a cylindrical recess 242 (pocket, channel). To enable magnetic coupling between the cable connector 232 and the patient monitor port 232', the protective wall 240 of the cable connector 232 may be thin and yet structurally sound.

The cable connector's recessed surface 241d has openings 243 that are completed filled (occupied) by respective electrical contacts 244. Each contact 244 has an exposed front surface 244c that is flush with the recessed surface 241d, leaving no gap (crevice) between the recessed surface 241d and the contact's front surface 244c. Each contact 244 is adjoined to an electric line 244b of the cable lead 30 (FIG. 1).

Figure 8A:
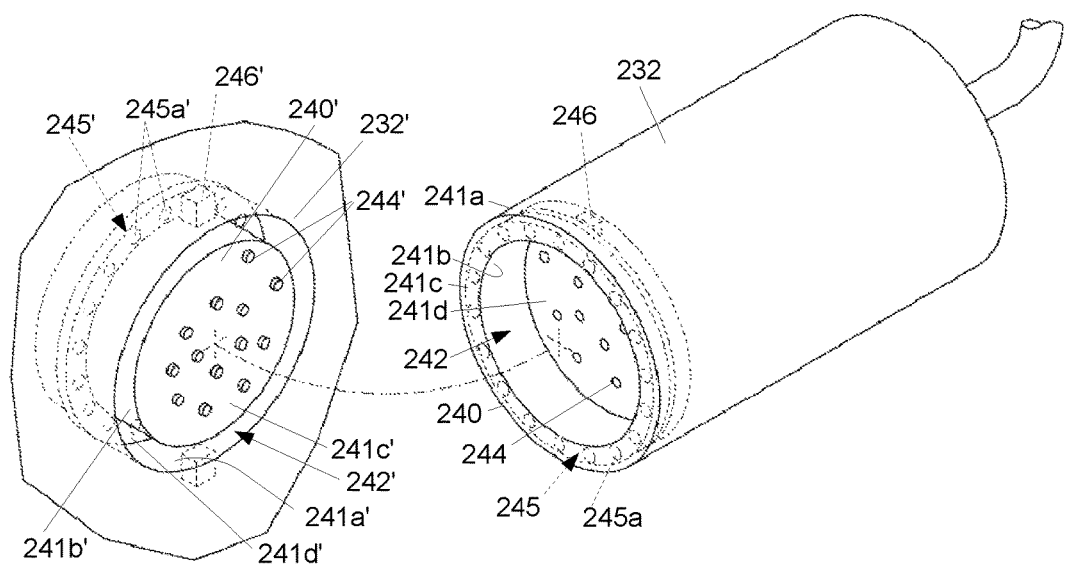
FIG. 8A is a perspective view of a connection port of the patient monitor and a corresponding connector of one of the cables.
Figure 8B:
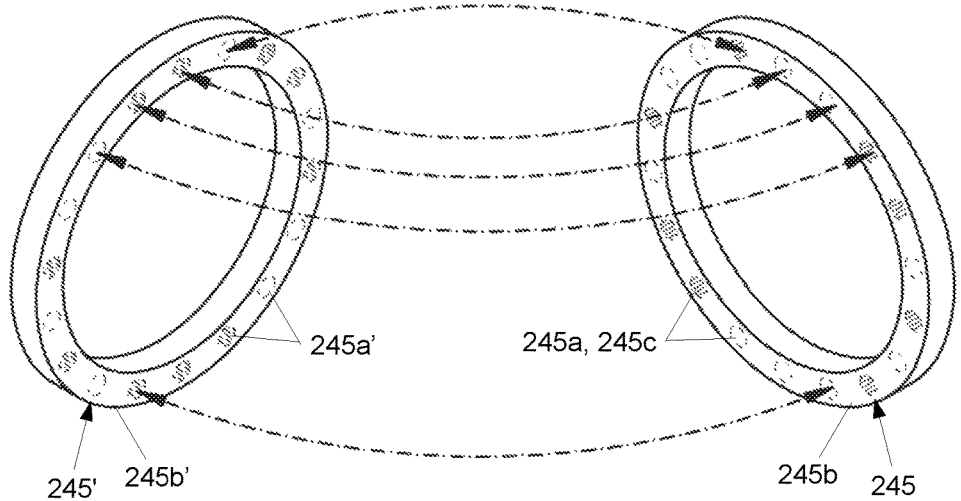
FIG. 8B is a perspective view of a magnet array of the connection port of FIG. 8A and a magnet array of the connector of FIG. 8A.
Figure 9:
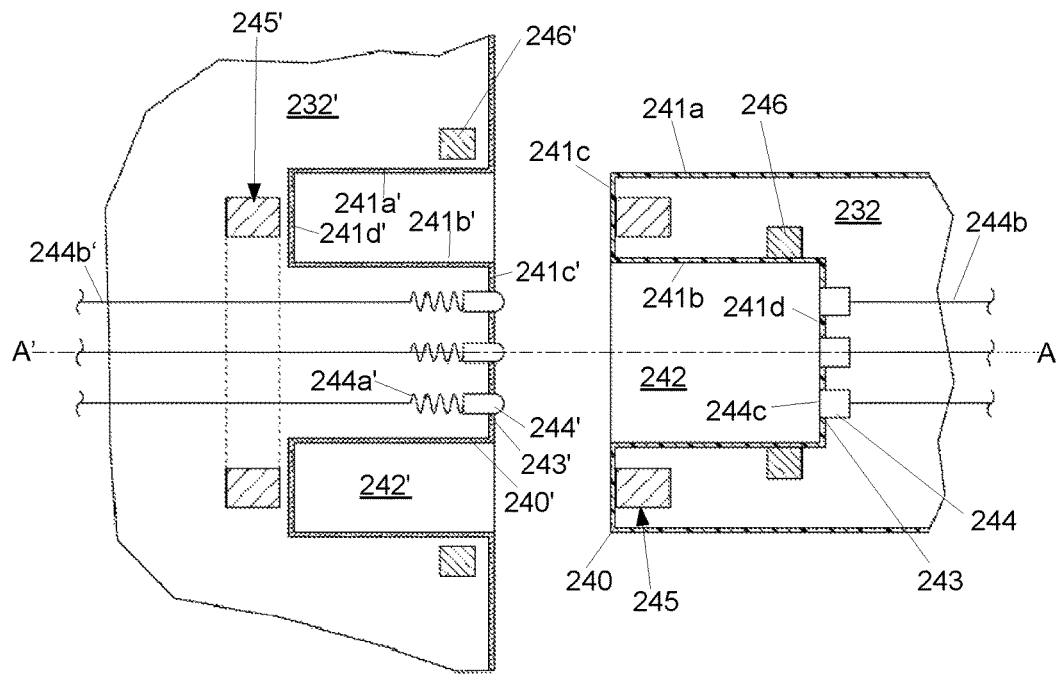
FIG. 9 is a sectional view of the patient monitor's connection port and the cable connector.

A circular array 245 of magnets 245a is located behind and protected by the cable connector's protective wall 240. The array magnets 245a are spaced apart along a circular path, and define a predetermined magnetic polarity pattern. The magnetic polarity pattern defines the positions of magnetic poles of the array magnets and may also define the magnetic field strength (intensity) of each magnet pole. The cable connector's array magnets 245a in this example comprise different magnetic regions (maxels) of a single piece of magnetizable material, to form a single cable connector multi-pole correlated magnetic (MPCM) structure in which the regions differ from each other in terms of magnetic polarity and/or magnetic strength. FIG. 8B includes an expanded view of the cable connector MPCM structure 245b, with all other components of the cable connector 232 omitted for clarity. The MPCM structure 245b is ring-shaped. Each magnetic region 245c (representing a respective magnet 245a) is cylindrical, and has a front periphery portrayed as a circle—a filled circle to portray a north pole, and an unfilled circle to portray a south pole. The cable connector's array magnets 245a may alternatively be separate permanent magnets or separate electromagnets, as described above for the patient monitor connector's array magnets 45a (FIG. 4). The patient monitor connector's array magnets 245a might be narrower than 2 mm, and might be spaced apart by less than 3 mm.

One or more ferromagnetic securing components 246, located behind the cable connector's protective wall 240, can be similar to any of the example magnetic securing components 46 of patient monitor connector 36 (FIG. 4).

The patient monitor port 232' is centered on a second axis A', about which walls and surfaces of the patient monitor port 232' are symmetric. Second axis A' is fixed relative to the patient monitor port 232'. The patient monitor port 232' includes a rigid insulating protective wall 240' that protects components of the patient monitor port 232' that are behind the protective wall 240'. The protective wall 240' provides (i) a cylindrical radially-outer surface 241a' facing radially-inward, (ii) a cylindrical radially-inner surface 241b' facing radially-outward, (iii) a forward-facing front surface 241c', and (iv) an annular forward-facing recessed surface 241d'. The radially-outer surface 241a', the radially-inner surface 241b', and the recessed surface 241d' together define a tubular recess 242' (pocket, channel). To enable magnetic coupling between the cable connector 232 and the patient monitor port 232', the protective wall 240' of the patient monitor port 232' may be thin and yet structurally sound.

The patient monitor port's front surface 241c' has openings 243' that are filled (occupied) by respective electrical contacts 244'. Each patient monitor port contact 244' is configured to contact a respective one of the cable connector's contacts 244. Each patient monitor port contact 244' is connected, via an electrical line 244b' within the patient monitor 10, to a circuit within the patient monitor 10. Each of the patient monitor port's contacts 244' is spring-loaded, by a spring 244a' within the patient monitor port 232', to be initially in an extended position in which the contact 244' projects beyond the front surface 241c'.

An array 245' of magnets 245a', behind the patient monitor port's recessed surface 241d', defines a magnetic polarity pattern. This polarity pattern of the port's magnet array 245' complements (in terms of position and opposite polarity) the cable connector's polarity pattern, in the same manner as explained above regarding the docking station port's polarity pattern complementing the patient monitor connector's polarity pattern.

In this example, the patient monitor port's array magnets 245a' are electromagnets that are individually programmed (activated, controlled) by the patient monitor controller 20. In another example, the port's array magnets 245a' might be separate permanent magnets, or might be maxels of a single MPCM structure. The array magnets 245a' in this example are integrated into a single ring 245b'. FIG. 8B shows the patient monitor port's ring 245b' of array magnets 245a', with all other components of the patient monitor port 232' omitted for clarity. The front face of each array magnet 245a' in FIG. 8B is portrayed as a circle—a filled circle to portray a north pole, and an unfilled circle to portray a south pole. Dashed double-ended arrows in FIG. 8B indicate which array magnets 245a of the cable connector 232 align with, and magnetically interact with, which array magnets 245a' of the patient monitor port 232'.

One or more securing magnets 246', in this example electromagnets, behind the patient monitor port's protective wall 240', may be positioned so as to be near and aligned with the cable connector's securing component 246 when the cable connector 232 is in its mounted position. The securing magnet 246' may be controlled (activated) by the patient monitor controller 20 in any of the manners described above regarding the securing magnet 46' of the docking station port 32'.

The cable connector 232 is configured to be inserted into the patient monitor port's recess 242' until the cable connector 232 reaches its mounted position on the patient monitor port 232'. When in the mounted position, the patient monitor port's tubular recess 242' closely receives the cable connector 232. The radially-outer surfaces 241a', 241a of the patient monitor port 232' and the cable connector 232 may engage (contact) each other. The radially-inner surfaces 241b', 241b of the patient monitor port 232' and the cable connector 232 may engage each other. The patient monitor port's recessed surface 241d' and the cable connector's front surface 241c abut each other. The patient monitor port's front surface 241c' and the cable connector's recessed surface 241d abut, or almost abut, each other. Each of the cable connector's array magnets 245a is near and aligned with a corresponding (complementary) one of the patient monitor port's array magnets 245a'. Abutment of each of the cable connector's contacts 244 against a respective one of the patient monitor port's contacts 244' pushes the respective patient monitor port's contact 244' rearward, against spring bias of the corresponding spring 244a'. The contacts 244, 244' thus interface with each other, to communicate electrical signals and electrical power to flow between the patient monitor port 232' and the cable connector 232.

Engagement between cylindrical surfaces of the cable connector 232 and the patient monitor port 232' forces the first and second axes A, A' to be collinear while the cable connector 232 is in the patient monitor port 232'. The patient monitor port's recess 242' is configured to closely receive the cable connector 232, to constrain the first and second axes A, A' (of the cable connector and the patient monitor port) to remain collinear while enabling rotation of the cable connector 232 about the first axis A while the cable connector 232 is within the patient monitor port's recess 242'.

During insertion of the cable connector 232, the magnetic interaction between the magnet arrays 245', 245 (of the patient monitor port 232' and cable connector 232) attracts the cable connector 232 axially toward and into its mounted position. Concurrently, during insertion and even after reaching the mounted position, magnetic interaction between the magnet arrays 245', 245 applies a torque to the cable connector 232, rotationally urging the cable connector 232 toward proper rotational alignment with the patient monitor port 232'. The torque might be achieved through either or both (i) attraction when the cable connector 232 is properly rotationally aligned and (ii) repulsion when the cable connector 232 is improperly rotationally aligned. The torque might be tactile in that the aligning can be sensed (felt) by a person inserting the cable connector 232 into the patient monitor port 232'. When the cable connector 232 reaches its mounted position, attraction between the magnet arrays 245, 245' retains the cable connector 232 in place with a force weak enough to enable withdrawal of the cable connector 232.

The magnetic attraction, repulsion and torque described above might be tactile, in that the magnetic attraction, repulsion and torque would be sensed (felt) by a person (user) connecting the connector to the port. The magnetic attraction, repulsion and torque might simulate the feel of (provide the user with a tactile feel of) a conventional spring mechanism, detente mechanism or keying mechanism, that tactilely indicates to the person whether the cable connector 232 is or is not oriented properly, and perhaps tactilely indicates to the person which direction to rotate the cable connector 232, and perhaps provides a tactile feeling of reaching a detente position when the mounted position is reached.

In another example, the magnetic guiding and aligning might be sufficiently strong to move—such as relocate (reposition) and rotate—the cable connector 232 toward and into the mounted position automatically without manual (i.e., human) assistance (e.g., without the user even touching the patient monitor).

When the cable connector 232 reaches its mounted position, the patient monitor controller 20 may activate the patient monitor port's securing magnet 246' to magnetically attract the cable connector's securing component 246, to secure the cable connector 232 in place. The magnetic securing force augments the retaining force between the magnet arrays 245, 245'. Later, the patient monitor controller 20 may deactivate (de-energize) the electromagnet 246' to release the cable connector 232. If the cable connector's magnetic securing component 246 is a magnet, the controller 20 may reverse the electromagnet's polarity to repel the securing component 246, and thus cable connector 232, out of the patient monitor port 232'. The securing may be prompted by the controller 20 sensing that the cable connector 232 reached its mounted position or in response to a human action. The sensing (of the cable connector reaching its mounted position) may be by the controller 20 receiving a predetermined signal (data communication) from the cable connector 232 via the electrical contacts 244', 244. The releasing may be prompted by the controller 20 determining that a test is completed or by a user's action.

Figure 10:
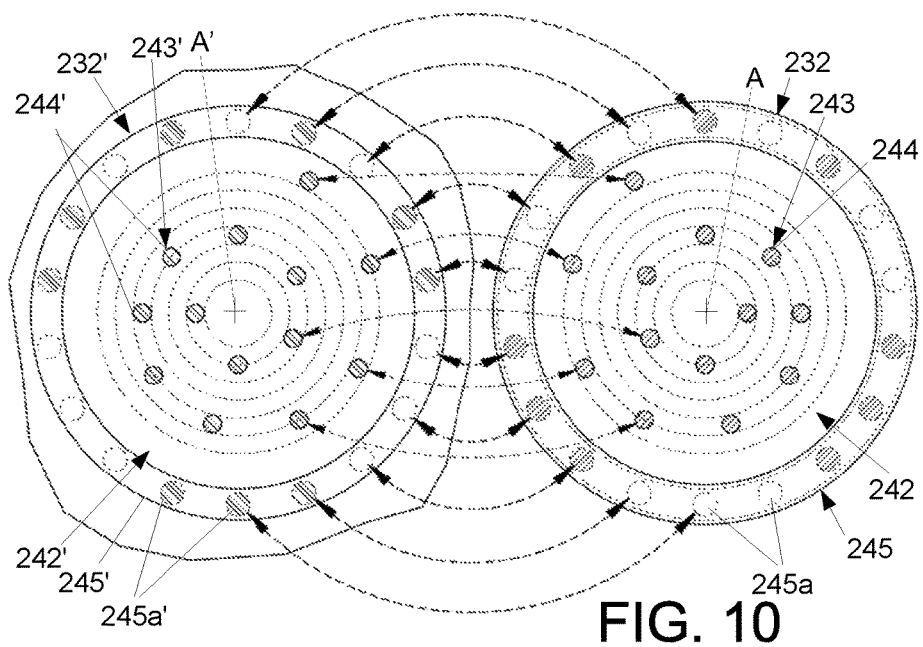
FIG. 10 includes a front view of the patient monitor's connections port and a front view of the cable connector.

FIG. 10 is a front view of the cable connector 232 and the patient monitor port 232', showing placement of the electrical contacts 244', 244. Dashed double-arrow lines indicate which contacts 244' of the patient monitor port 232' contact which contacts 242 of the cable connector 232. The contacts 244, 244' are spaced apart along a spiral path that spirals radially outward from the respective axis A, A'. Each contact 244, 244' has a radial distance from the respective axis A, A'. Each contact's radial distance differs from each other contact's radial distance. This prevents any contact 244 of the cable connector 232 from contacting the wrong (non-corresponding) contact 244' of the patient monitor port 232' as the cable connector 232 rotates into proper alignment. The spiral configuration enables a higher contact density compared to if the contacts were spaced apart along a common radius line. In accordance with the spiral configuration, the contacts' radius values are a monotonic function of the contacts' angle about the axis. The monotonic function might be a linear function. For example, the contacts 244, 244' might be spaced apart by a set angular increment (e.g., 45 degrees) and a set radial distance increment. The spiral path might extend from the radially-inward-most contact to the radially-outward-most contact. The spiral path might extend, for example, as little as 10 degrees about the axes A, A' or might extend multiple (e.g., three) revolutions about the axes A, A'.

The patient monitor port's polarity pattern might complement the magnet pattern of only a specific one of the cable connectors 232, so as to attract and align that specific cable connector and to not attract, and perhaps even repel, the other cable connectors.

If the patient monitor port's array magnets 245a' are electromagnets, then the magnetic polarity pattern can be reprogrammed by the patient monitor's controller 20 during use. For example, one patient monitor port might be programmed to attract only one of the cable connectors 232 at one point in time and to be reprogrammed to attract only another one of the cable connectors 232 at another point in time. For example, if a user enters (inputs) into the patient monitor 10 a selection (device setting) that the patient is a child, for the patient monitor 10 to enter a device state configured for child oximetry, then the port 232' that is configured to be connected to an oximeter cable will be re-programmed by the patient monitor controller 20 to attract only an oximeter cable whose finger sensor is sized for a child.

In another example, the patient monitor 10 can, to minimize size, be designed to have one patient monitor port accept multiple cables—such as both an ECG cable and an oximeter cable. If a user inputs a selection (device setting) to perform an ECG test, for the patient monitor 10 to enter a device state configured for ECG testing, then the patient monitor port's array magnets 245a' would be programmed by the patient monitor controller 20 to attract only an ECG cable and the securing magnets 46' would be controlled by the patient monitor controller 20 to secure only the ECG cable. Later, if a user inputs a selection to perform an oximeter test, then the port's magnet array 245' would be reprogrammed by the controller 20 to attract only an oximeter cable and the securing magnets 246' would be controlled to secure only an oximeter cable.

For the patient monitor port's array magnets 245a' to be programmable, the patient monitor controller 20 might be able to reverse the polarity of each array magnet 245a' individually by reversing the direction of electrical supply current to that magnet 245a'. The patient monitor controller 20 might also adjust magnetic field strength of each array magnet 245a' individually, by adjusting the magnitude of the electrical supply current to that array magnet 245'.

Figure 11:
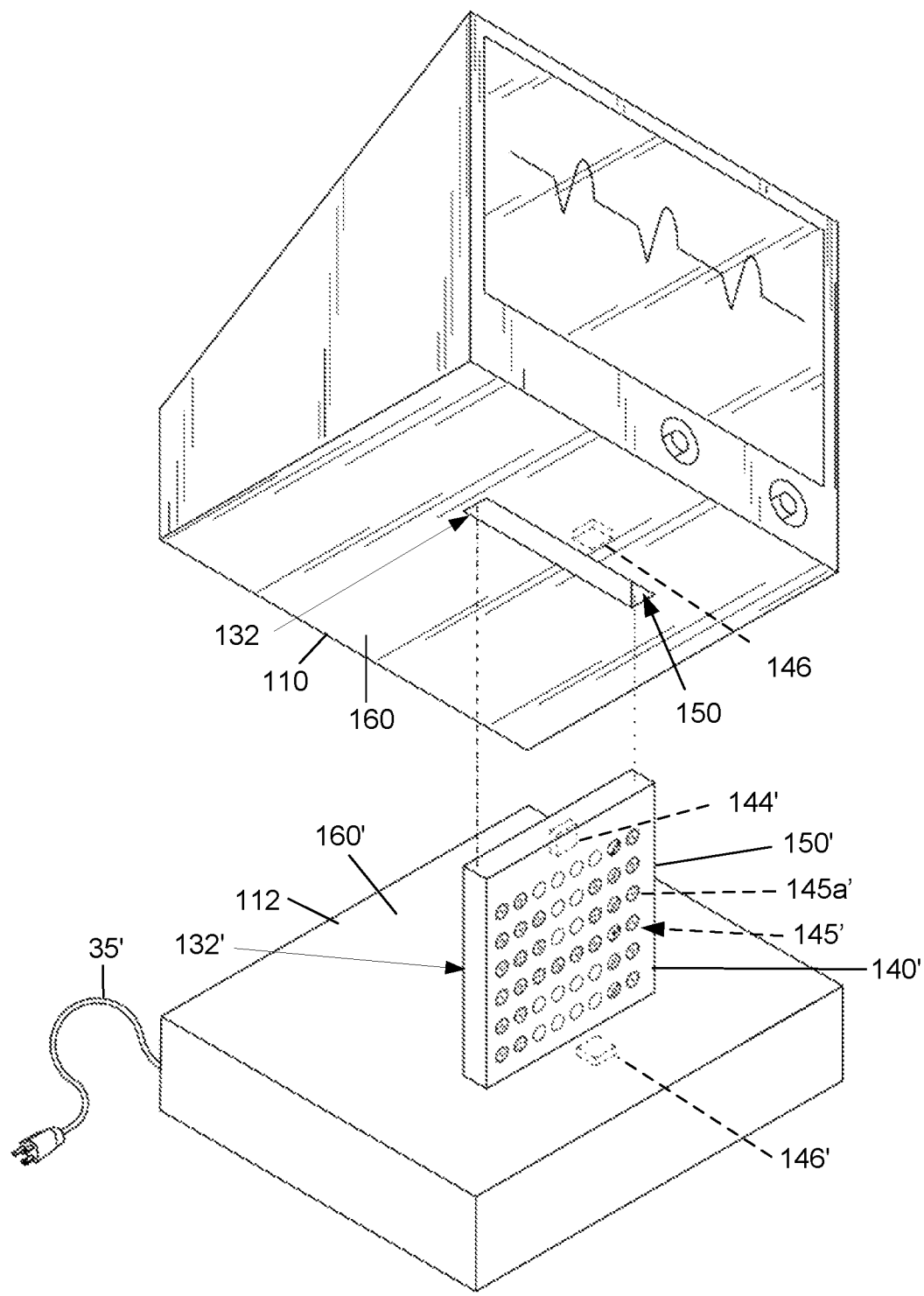
FIG. 11 is a perspective view of another example apparatus, in which a second patient monitor mounts on a second docking station in a tab-in-slot configuration.
Figure 12:
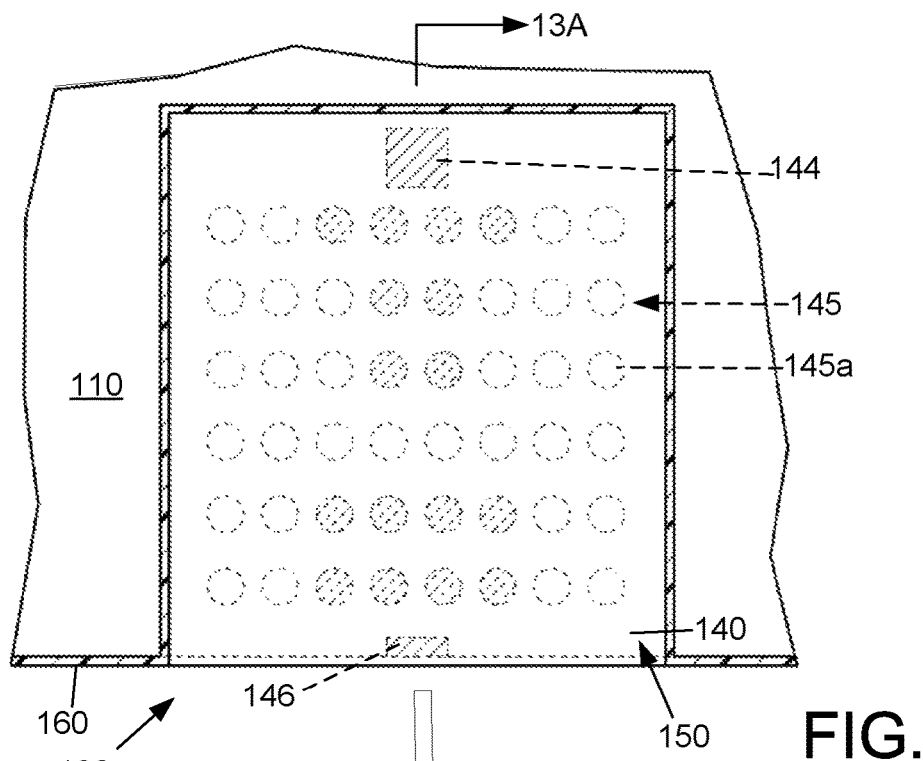
FIG. 12 is a front sectional view of the second patient monitor located above the second docking station.
Figure 12:
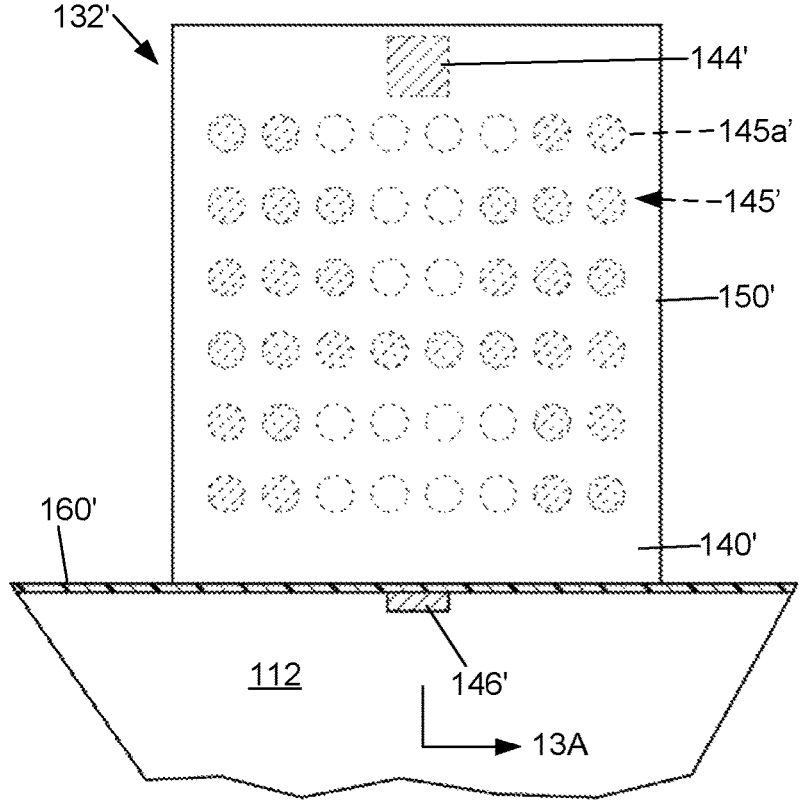
Figure 13C:
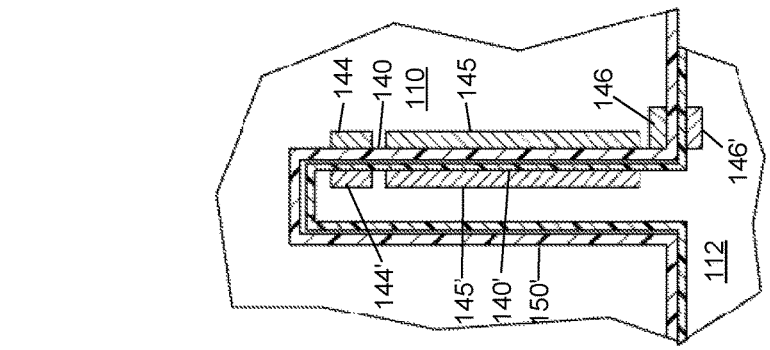
FIG. 13C is a sectional view similar to FIG. 13B, showing the second patient monitor in the mounted position on the second docking station.
Figure 13B:
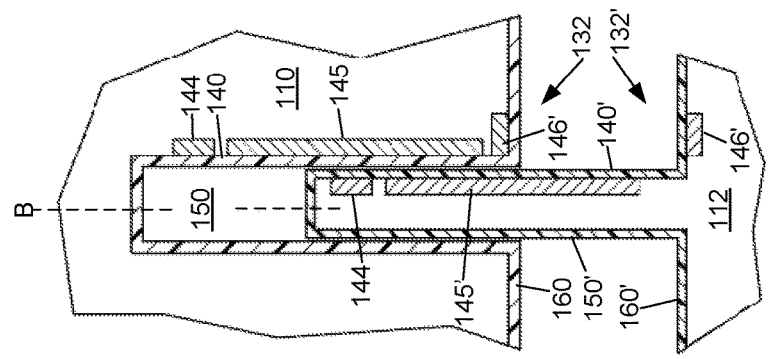
FIG. 13B is a sectional view similar to FIG. 13A, showing the second patient monitor being moved toward a mounted position on the second docking station.
Figure 13A:
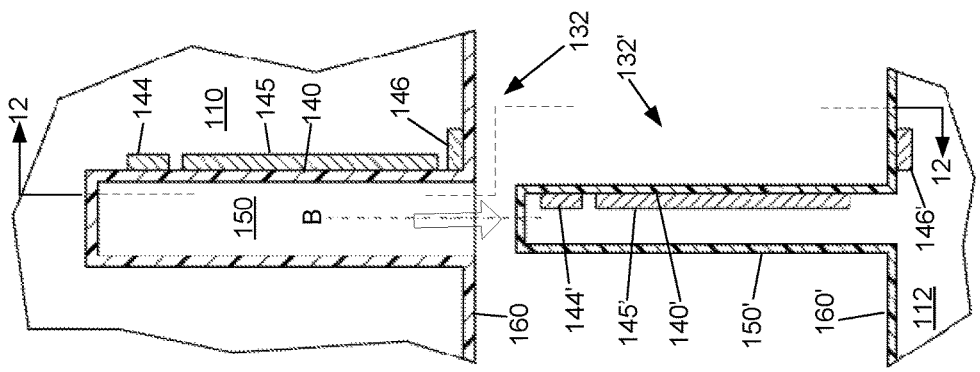
FIG. 13A is a side sectional view taken at line 13A-13A of FIG. 12.

FIGS. 11-12 and 13A illustrate a second example of a patient monitor 110 (second patient monitor) and a corresponding docking station 112 (second docking station). This second example has components that correspond with the components of the first example (FIGS. 1-4). In the figures, components of this second example are assigned reference numerals that correspond to reference numerals of corresponding components of the first example, but with a "1" digit in the hundredth's place.

The docking station port 132' of the second docking station 112 has an upward-projecting tab 150' (projection). A vertical section of the docking station port's protective wall 140' extends vertically along a side of the tab 150'. An array 145' of magnets 145a' extends vertically behind the vertical section of the docking station port's protective wall 140'. A securing magnet 146' is located behind the protective wall 140' (in this example behind a horizontal section of the protective wall 140'). The securing magnet 146' is an electromagnet controlled by the docking station controller 20' (FIG. 1), North poles (facing toward the reader) are portrayed with filled-in circles and south poles (facing toward the reader) are portrayed with unfilled circles. In this example, each of the port's array magnets 145a' is an electromagnet that is independently activated by the docking station controller 20' (FIG. 1). The magnetic polarization pattern of the docking station port's array 145' is therefore programmable, in that the docking station controller 20' can control the polarity and magnetic strength of each array magnet 145' individually.

The patient monitor connector 132 of the second patient monitor 110 includes an upward-extending a slot 150 (channel) configured to be slid down over the docking station port's tab 150' and to closely receive the docking station port's tab 150'. The slot 150 is bounded by a vertical portion of a protective wall 140. A vertically-extending array 145 of magnets 145a is located behind the vertical portion of the protective wall 140. The patient monitor connector's magnet array 145 has a polarity pattern that is complementary to the polarity pattern of the docking station port's magnet array 145', so as to magnetically attract the patient monitor connector's array 145 to a mounted position in which each patient monitor connector array magnet 145 is adjacent and aligned with a complementarily-polarized docking station port array magnet 145'. The patient monitor connector's array magnets 145 may be formed of discrete permanent magnets or of different magnetic regions of a single magnetizable piece of material.

Magnetic interaction between the magnet arrays 145, 145' might replicate the tactile feeling (by a user) of a spring force that acts against the insertion of the patient monitor connector 132, such that the patient monitor's weight is reduced upon insertion, and yet allows the patient monitor 110 to be fully docked without burden to the user.

The magnitude of this spring force can be varied along the direction of mounting (i.e., the vertical direction that the patient monitor connector 132 moves when moving toward the mounted position) by populating the array magnets 145a, 145a' such that the net resultant force of attraction and/or repulsion from each row of the magnet array 145, 145' can vary. A force normal to the direction of mounting may have sufficient lateral/shear hold attraction or repulsion to realize a tactile spring effect. The second patient monitor 110 reaches its mounted position when the patient monitor's bottom surface 160 abuts a top surface 160' of the second docking station 112. Concurrently, an optical or electrical terminal 144 of the patient monitor 110 interfaces with a corresponding optical or electrical terminal 144' of the second docking station 112 for data communication and/or power transmission between the docking station 112 and the patient monitor 110.

FIGS. 13A-13C illustrate a sequence of positions that the patient monitor connector 132 is in while being mounted on the docking station port 132'. FIG. 13A shows the patient monitor connector 132 moving downward toward its mounted position (i.e., the position of FIG. 13C). In FIG. 13B, the patient monitor connector's slot 150 receives the docking station port's tab 150' as the patient monitor connector 132 moves downward in a linear motion along an axis B that is fixed relative to the docking station port 132'. In the final mounted position, shown in FIG. 13C, the patient monitor connector's magnet array 145 is directly facing and aligned with the docking station port's magnet array 145', in that each of the patient monitor connector's array magnets 145a is directly facing and aligned with a corresponding one of the docking station port's array magnets 145a'. Concurrently, the patient monitor connector's securing component 146 overlies the docking station port's securing magnet 146'. When the docking station controller 20' (FIG. 1) detects that the patient monitor 110 is in the mounted position, the docking station controller 20' (FIG. 1) activates the securing magnet 146' to attract the patient monitor connector's securing component 146, to secure the patient monitor connector 132 (and thus also the patient monitor 110) in place.

The determination by the second example docking station 112 that the second example patient monitor 110 has reached its mounted position may be through the example magnetic sensing described above by which the first example docking station 12 determines that the first example patient monitor 10 reached its mounted position. If the terminals 144, 144' are optical, then the determination may be through the example optical sensing described above by which the first example docking station 12 determines that the first example patient monitor 10 reached its mounted position. If the terminals 144, 144' are electrical contacts, then the determination may be through electrical data signals communicated between the first example docking station 12 and the patient monitor 10 via the terminals 144, 144' (electrical contacts).

Accordingly, the patient monitor connector's slot 150 closely receives the tab 150' of the docking station port 132', to enable linear movement of the docking station port 132' while preventing lateral movement of the patient monitor connector 132 relative to the docking station port 132'. In this configuration, the port array 145 extends along a port array plane, and the connector array 145' extends along a connector array plane. The apparatus is configured to, when the patient monitor connector 132 is moved toward and into the mounted position on the docking station port 132', constrain the port array plane and the connector array plane to be parallel with each other and parallel with direction of movement of the patient monitor connector 132 toward and into the mounted position.

The controller 120' can later release the patient monitor connector 132 by deactivating the securing magnet 146'. If the patient monitor connector's securing component 132 is a magnet, the docking station controller 20' can reverse the electrical supply current to the docking station port's securing magnet 146' to reverse the securing magnet's polarity to repel the patient monitor connector's securing component 146, and thus the patient monitor 110 upward and away from the mounted position.

This second example differs from the first example in the following ways: The magnet arrays 145', 145 and the protective walls 140', 140 extend vertically, which is the direction that the patient monitor moves when moving toward the mounted position. This is in contrast to the first example, in which the magnet arrays and the protective walls extend horizontally, which is perpendicular to the direction that the patient monitor moves when moving toward the mounted position. Also, in this second example, the magnet arrays 145', 145 move alongside each other when the patient monitor 110 is being moved toward its mounted position. This is in contrast to the first example, in which the magnet arrays move, face-to-face, toward each other. In the second example, a tab-in-recess configuration enables linear movement of the patient monitor connector along axis B (enables movement in only one direction) toward the mounted position, while preventing lateral and rotational movement of the connector relative to the port. Accordingly, the docking station port and the patient monitor connector are configured to enable movement of the patient monitor connector in only a single fixed direction toward and into the mounted position.

Figure 14A:
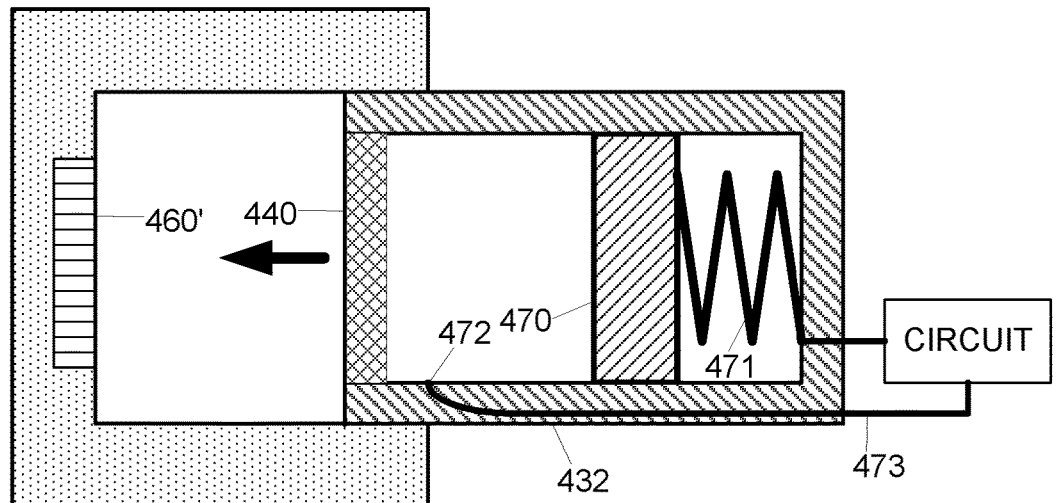
FIG. 14A-14B are sectional views of an electric switch arrangement that can be included in a connector, with the connector shown respectively in an unmounted position and a mounted position.

FIG. 14A shows an example electric switch arrangement that can be added to a connector 432, such as any of the connectors described above. The connector 432 is configured to be mounted to a port 432', such as any of the ports described above.

This electrical switch arrangement includes a ferromagnetic movable component 470 that is located behind a protective wall 440 of the connector 432 (such as any protect wall described above) and that is spring-biased (urged by spring bias), by a spring 471, away from the protective wall 440 in an initial retracted position. The movable component 470 is made of a ferromagnetic material (e.g., steel) that is attracted to a magnet 460 in a port 432'.

FIG. 14A shows the connector 432 in an unmounted position, separated from the port 432'. When the cable connector 432 is near, or is in, the mounted position, the movable component 470 is attracted to the magnet 460' in the port 432'. The magnet in the port 432' can be the port's magnet array 245' or the port's securing magnet 246' or some other magnet in the port 432'. The magnetic attraction moves the movable component 470, against the spring bias of the spring 471, toward both the port's magnet 460' into an extended position shown in FIG. 14B. Movement of the movable component 470 may open or close an electrical circuit. For example, the moveable component 470 might contact an electrical contact 472 to complete a circuit 473 when in the extended position, and be spaced away from the electrical contract 472 when in the not extended position, or vice versa. When the circuit 473 is completed, electricity might flow through the spring 471 and through the movable component 470 to the contact 472. The movable component 470 thus functions as an electronic switch mechanism.

Figure 14B:
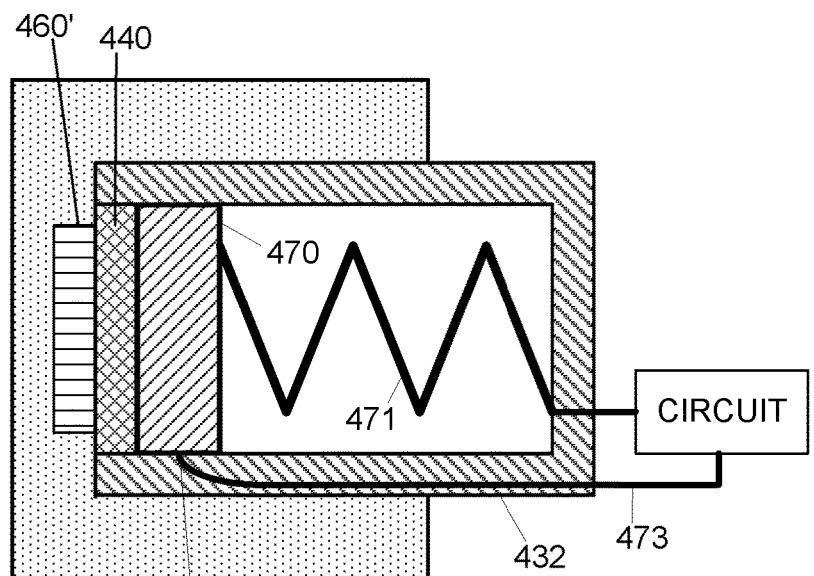

In the above example of FIGS. 14A-14C, the electrical switch arrangement is included in one of the connectors, to open or close a circuit in the connector when the connector is in the mounted position. In another example, the electrical switch arrangement may be included in one of the ports, to open or close a circuit in the port when the connector is in the mounted position.

In the above example, a single controller 20, 20' (in the docking station or the patient monitor) comprises, and functions as, both a securing magnet controller that controls activation of the respective port's securing magnet and (ii) a port array controller that controls activation of the respective port's array magnets. Accordingly, the securing magnet controller and the port array controller may comprise the same controller.

In some instances in the above description, a term is followed by an alternative term or a substantially equivalent term enclosed in parentheses.

In the above example, the ports and connectors have no crevices, cracks or gaps, because they have a continuous protective wall with a smooth outer surface. This helps avoid ingress of dirt, and facilitates cleaning of the ports and connectors.

In the above examples, the guiding, aligning and securing of each connector to the respective port might be solely by magnetic force, without any mechanical guiding or securing means. That magnetic force may be provided solely by the array magnets and the securing magnet.

Electromagnets included in the above examples, whether in the magnet arrays or the securing magnets, may include an electropermanent magnet that retains its magnetism even when current is removed. That would avoid the need for the respective controller to power the respective electromagnet continuously the entire time the electromagnet needs to be magnetically polarized.

In the examples above, the securing magnets 46', 146', 246' are electromagnets that are activated by being electrically energized to attract the corresponding securing component 46', 146', 246'. In other examples, any of the securing magnets 46', 146', 246' may instead be a movable permanent magnet that is activated by being moved toward, and sufficiently near, the corresponding securing component 46', 146', 246' to securing the securing component in place. The position of the moveable permanent magnet might be adjusted by a linear motor that is within the respective device (docking station or the patient monitor) and that is controlled by the respective controller. To secure each connector 32, 132, 232 to the respective port, the motor would move the port's moveable permanent magnet close to the connector's securing component. To release the connector from the port, the motor would deactivate the port's moveable permanent magnet by moving the port's moveable permanent magnet sufficiently away from the connector's securing component to release the securing component. A possible advantage of this moveable permanent magnet configuration over the electromagnet configuration is that it does not require an electromagnet-energizing electrical current to flow through the magnet, which might electromagnetically (inductively) interfere with electrical signals being communicated between the port and connector.

The ports and connectors in the above example connect a patient monitor to a docking station and connect cables to the patient monitor. In another example, the port and connector may provide connectivity for other apparatuses and purposes. Any port described above may be a part (component) of a patient monitor or a part of a docking station or a part of a cable. Similarly, any connector described above may be a part of a patient monitor or a part of a docking station or a part of a cable.

Although the example ports and connectors described above provide connectivity for interfacing electrical and optical terminals for communicating electrical and optical signals, interfacing of other terminals may be possible, such as interfacing fluid (e.g., pneumatic) ports.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

The invention claimed is:

1. An apparatus comprising:
a port configured for connection with a first connector that includes a first connector array of magnets having a first connector magnetic polarity pattern, the port including:
a port array of magnets, each magnet of the port array of magnets having a magnetic polarity, the port array of magnets being configured in a first port magnetic polarity pattern that is complementary to the first connector magnetic polarity pattern so as to guide and align the first connector toward a mounted position in which the first connector is retained on the port, wherein the guiding and the aligning is through both (i) attraction when the first connector is properly aligned to the port and (ii) repulsion when the first connector is improperly aligned to the port;

a securing magnet configured to be activated when the first connector reaches the mounted position, to magnetically secure the first connector to the port,
wherein the apparatus further comprises
a port array controller configured to change the port array of magnets to a second port magnetic polarity pattern that is different from the first port magnetic polarity pattern, wherein the second port magnetic polarity pattern is complementary to a second connector magnetic polarity pattern of a second connector array of magnets of a second connector configured for connection with the port, thereby enabling the port to accept only a connector having the second port magnetic polarity pattern, and wherein the magnetic polarity of at least one magnet of the port array of magnets is reversed when the port array of magnets is changed from the first port magnetic polarity pattern to the second port magnetic polarity pattern.

2. The apparatus of claim 1, further comprising at least one of the first connector and the second connector.

3. The apparatus of claim 2, wherein at least one of the first connector and the second connector is configured to be secured to the port solely by (i) magnetic force between a corresponding one of the first and second connector arrays of magnets and the port array of magnets and (ii) magnetic force of the securing magnet.

4. The apparatus of claim 2, wherein at least one of the first connector and the second connector includes a permanent magnet securing component that is configured to be attracted to the securing magnet when the securing magnet is activated to have a first polarity and to be repelled from the securing magnet when the securing magnet is activated to have an opposite second polarity.

5. The apparatus of claim 2, wherein at least one of the first connector and the second connector includes a connector terminal and the port includes a corresponding port terminal, for communicating signals between the port terminal and the connector terminal.

6. The apparatus of claim 5, wherein at least one of the first connector and the second connector includes a connector protective wall behind which the corresponding one of the first and second connector arrays of magnets and the connector terminal are located.

7. The apparatus of claim 2, further comprising a port axis that is fixed relative to the port and a connector axis that is fixed relative to at least one of the first connector and the second connector, and wherein the port and the connector are together configured to require the axes to be collinear while the connector moves toward and into the mounted position, while enabling the connector to rotate about the axes.

8. The apparatus of claim 2, wherein the port and at least one of the first connector and the second connector together include a tab-in-recess configuration configured to enable linear movement of the connector toward and into the mounted position on the port while preventing lateral and rotational movement of the connector relative to the port.

9. The apparatus of claim 2, wherein the attraction between the port array of magnets and at least one of the first connector array of magnets and the second connector array of magnets is tactile.

10. The apparatus of claim 1, further comprising a securing magnet controller, and
wherein the securing magnet comprises an electromagnet that is configured to be activated by the securing magnet controller electrically energizing the securing magnet to secure at least one of the first connector and the second connector.

11. The apparatus of claim 10, wherein the securing magnet is configured to release at least one of the first connector and the second connector by being electrically de-energized.

12. The apparatus of claim 10, wherein the securing magnet is configured to repel at least one of the first connector and the second connector by the securing magnet controller reversing activation current through the securing magnet.

13. The apparatus of claim 10, wherein the securing magnet controller is configured to (i) activate the securing magnet to have a first magnetic polarity to secure at least one of the first connector and the second connector to the port, and (ii) reverse the polarity of the securing magnet to magnetically repel at least one of the first connector and the second connector from the port.

14. The apparatus of claim 10, wherein the securing magnet controller is configured to activate the securing magnet automatically in response to at least one of the first connector and the second connector reaching the mounted position.

15. The apparatus of claim 10, wherein the securing magnet controller is configured to activate the securing magnet automatically in response to a human action.

16. The apparatus of claim 1, wherein the securing magnet comprises a movable permanent magnet configured to (i) be activated by being moved toward at least one of the first connector and the second connector and (ii) be deactivated by being moved away from at least one of the first connector and the second connector.

17. The apparatus of claim 1, wherein the port includes a port terminal, for communicating signals between the port and at least one of the first connector and the second connector, wherein the signals are electrical or optical.

18. The apparatus of claim 17, wherein the port includes a protective wall behind which the port array of magnets, the securing magnet and the port terminal are located.

19. The apparatus of claim 17, wherein the port terminal is one of a spiral array of port terminals that the port has for communicating signals between the port and at least one of the first connector and the second connector.

20. The apparatus of claim 1, wherein the magnets in the port array of magnets are narrower than 2 mm.

21. The apparatus of claim 1, wherein the magnets of the port array of magnets are electromagnets and activated by the port array controller.

22. The apparatus of claim 21, wherein the port array controller is configured to adjust magnetic field strength of one or more of the magnets of the port array of magnets individually.

23. The apparatus of claim 1, wherein the port array controller is configured to change magnetic polarities of the port array of magnets to a third port magnetic polarity pattern, that is configured to not provide the attraction to a second port array.

24. The apparatus of claim 23, wherein the port is part of a patient monitoring device, and the port array controller is configured to change the magnetic polarities of the port array of magnets based on a device setting of the patient monitoring device.

25. The apparatus of claim 23, wherein the port is part of a patient monitoring device, and the port array controller is configured to change the magnetic polarities of the magnets of the port array of magnets based on a device state of the patient monitoring device.

26. The apparatus of claim 1, wherein the second connector magnetic polarity pattern is complementary to the second port magnetic polarity pattern, so as to guide and align the second connector, through both (i) attraction when the second connector is properly aligned and (ii) repulsion when the second connector is improperly aligned, toward a predetermined mounted position against the port.

27. The apparatus of claim 1, wherein the port includes a cylindrical recess that surrounds and bounds a planar front surface, and wherein a signal terminal is located along the front surface, and the port array of magnets is located behind a recessed surface at a bottom of the recess.

28. The apparatus of claim 1, wherein the port array of magnets extends along a port array plane, and the connector array of magnets extends along a connector array plane, and the apparatus is configured to constrain the port array plane and the connector array plane to be parallel with each other and parallel with direction of movement of the connector toward and into the mounted position on the port.

29. The apparatus of claim 1, wherein the guiding and aligning are sufficiently strong to move at least one of the first connector and the second connector into the mounted position automatically without manual interaction.

30. The apparatus of claim 1, wherein the port is a part of a patient monitor.

31. The apparatus of claim 1, wherein the port is a part of a cable.

32. The apparatus of claim 1, wherein the port is a part of a docking station.

33. The apparatus of claim 1, wherein at least one of the first connector and the second connector is a part of a patient monitor.

34. The apparatus of claim 1, wherein at least one of the first connector and the second connector is a part of a cable.

35. The apparatus of claim 1, wherein at least one of the first connector and the second connector is a part of a docking station.

36. The apparatus of claim 1, further comprising a ferromagnetic movable component that is urged by a spring bias into a retracted position, and that is configured to be attracted by a magnet in the port to move, against the spring bias, into an extended position when at least one of the first connector and the second connector is in the mounted position;
    wherein:
        the movement of the ferromagnetic movable component is configured to open or close an electrical circuit, and
        the ferromagnetic movable component is in the port and/or in at least one of the first connector and the second connector.

37. The apparatus of claim 1, wherein one or more of the magnets of the port array of magnets comprises an electropermanent magnet.

38. The apparatus of claim 1, wherein the securing magnet comprises an electropermanent magnet.

\* \* \* \* \*